(12) United States Patent
Deck

(10) Patent No.: US 7,595,873 B1
(45) Date of Patent: Sep. 29, 2009

(54) RAPID SPATIAL AVERAGING OVER AN EXTENDED SAMPLE IN A RAMAN SPECTROMETER

(75) Inventor: Francis J. Deck, Madison, WI (US)

(73) Assignee: Thermo Electron Scientific Instruments LLC, Madison, WI (US)

( * ) Notice: Subject to any disclaimer, the term of this patent is extended or adjusted under 35 U.S.C. 154(b) by 121 days.

(21) Appl. No.: 12/029,427

(22) Filed: Feb. 11, 2008

(51) Int. Cl.
*G01J 3/44* (2006.01)
*G01N 21/65* (2006.01)
(52) U.S. Cl. ..................................... 356/301
(58) Field of Classification Search .................. 356/301
See application file for complete search history.

(56) References Cited

U.S. PATENT DOCUMENTS 5,329,352 A * 7/1994 Jacobsen .................... 356/301
7,102,746 B2 * 9/2006 Zhao .......................... 356/301
2003/0007145 A1 * 1/2003 Shimada ..................... 356/301

* cited by examiner

*Primary Examiner*—F. L Evans
(74) *Attorney, Agent, or Firm*—Michael C. Staggs

(57) ABSTRACT

An optical method and apparatus is utilized to provide rapid spatial averaging over a large sample area in a Raman spectrometer, without defocusing of the optical source or the collection optics. Spatial averaging provides a representative spectrum of a sample that is inhomogeneous, either in its composition or surface characteristics. The spatial averaging configurations and methods disclosed herein also reduce sample degradation or burning resulting from the high intensity of the directed optical source. Moreover, the dimensions of the sample area of the spatial averaging methods and configurations of the present invention are adjusted to match specific sampling requirements.

22 Claims, 2 Drawing Sheets

RAPID SPATIAL AVERAGING OVER AN EXTENDED SAMPLE IN A RAMAN SPECTROMETER

BACKGROUND OF THE INVENTION

1. Field of the Invention

The present invention relates to optical spectroscopy. More particularly, the present invention relates to a dispersive Raman scanning method and apparatus for characterizing materials.

2. Discussion of the Related Art

When illuminating light, such as a laser beam, is incident upon a sample material, molecular bonds in the material can be excited by the incident light and can emit radiation which can be detected as scattered light. The Rayleigh component of the scattered light corresponds to the light emitted when the molecule relaxes from the excited state to the ground state. Infrequently, the molecule relaxes to a different vibrational or rotational level in the ground state. This produces Raman scattering components at Stokes and Anti-Stokes frequencies. A sample composed of multiple molecular species will produce a spectrum of such Raman scattering. The Raman scattering components can be detected and analyzed to help determine the composition of the sample.

Various apparatus have been developed for analyzing Raman spectra including Raman microscopes in which a very small area on a sample can be analyzed to determine characteristics of the composition of the sample at that area. In a typical Raman microscope, narrow band or monochromatic illuminating light, such as from a laser, is passed along a beam path through the objective lens of the microscope where it is focused at a focal point on a specimen. The Raman scattering from the sample collected by the microscope objective is passed back on a beam path to a spectrograph which typically separates the Raman scattering radiation by wavelength and detects it. Optical elements are typically included in the excitation beam path and the returning Raman radiation beam path to separate the excitation light from the Raman scattering light and to filter out the Rayleigh light from the beam directed to the spectrograph.

With respect to confocal dispersive spectroscopy, the excitation source is typically brought to a focus at the sample through an objective lens that is also the objective for collecting a resultant scattered radiation, such as, for example Raman-scattered radiation. Thus, the laser and the collected light follow the same beam path but in opposite directions, even when this beam path is deflected. For measurements over a small area, a dispersive confocal Raman spectrometer can be utilized due to the presence of two apertures in such a system. If the optical source, i.e., the laser source, is configured to operate in a single transverse spatial mode (a "high brightness" laser), then such a configuration provides for an effective aperture once it is focused to a desired diffraction limited spot size at the sample plane. Due to the confocal configuration, a second aperture, at the entrance of the spectrograph, defines a small field of view of the sample plane. These properties, while beneficial, cause a problem when attempting to characterize materials that are inhomogeneous, either in their composition, or in their surface properties. In such an arrangement, the measured spectrum changes when the sample is moved by a small amount, or when attempting to characterize different samples of the same composition. The user of the instrument is thus faced with deciding whether the samples are different, or if the apparent difference is an artifact of the measurement.

A typical method for solving the inhomogeneous problem discussed above often includes defocusing the optical laser source, the spectrograph, or both. However, defocusing the source and/or the spectrograph reduces the amount of light entering the spectrograph aperture, which thus degrades the sensitivity of the instrument. Moreover, a variable defocus mechanism varies the sensitivity and often is complex as well as cost ineffective. An alternate solution is to scramble the laser and spectrograph beams, for example, by using diffusers or multi-mode optical fibers but such methods have the same drawback as defocusing.

Another method that has been utilized to resolve the aforementioned problem includes anamorphic defocusing, which involves using optical elements (e.g., prisms, cylindrical lenses) to defocus the optical source in a direction oriented to the image of the spectrograph entrance slit. Such elements can define a linear field of view but cannot cover an extended area unless defocusing is also used. In addition, extending the field of view beyond a few tens of microns under a typical objective lens extends the collected image beyond the length of a typical spectrograph slit, which also results in a loss of sensitivity.

Another common method to resolve the inhomogeneous sample problem is to spin or move the sample. However, such a method has the drawback of complexity and cost because samples can be of arbitrary size and geometry. Furthermore, such a method is slow, unless the motion imposed on the sample is fast enough to potentially dislodge some types of samples such as powders.

Accordingly, a novel Raman spectrograph solution to optically characterize materials that are inhomogeneous as well as homogeneous is needed. The present invention is directed to such a need.

SUMMARY OF THE INVENTION

In accordance with the present invention, an optical apparatus is utilized to provide rapid spatial averaging over a large sample area by utilizing configured X-Y scanning mirror(s) to provide for angular displacement and an objective lens configured to focus and spatially displace such angularly displaced radiation so as to induce a desired emission in a Raman spectrometer. The spatial averaging configurations disclosed herein also reduce sample degradation or burning resulting from the high intensity of the directed optical source. Moreover, the dimensions of the sample area of the spatial averaging are adjusted to match specific sampling requirements.

Another aspect of the present invention is directed to a Raman spatially averaging method that includes: providing drive signals in a prime ratio to at least one X-Y scanning mirror so that an angularly displaced beam of light from an illumination source can be produced; spatially displacing via a focusing objective lens, the angularly displaced illumination beam of light so that a desired area of a sample can be scanned to induce Raman light in a time dependent manner; and spatially averaging the detected induced Raman light from the scanned desired area so that spectrally resolved information can be assessed.

Accordingly, the present invention provides for Raman configurations and methods that enable the collection of spectra that are representative of homogeneous and more often of inhomogeneous materials, or samples with complex surface texture, with minimal loss of sensitivity and without sample burning and radiation damage. In addition, such configurations provide for better sample-to-sample repeatability due to the averaging over microscopic surface features. Moreover, the collection of spatially averaged spectra in short exposure times of less than about 1 second enables the present invention to support high-throughput sampling, such as, for example, the sampling of micro-well plates. Finally, the dimensions of the sampling area can be user-adjustable to handle odd shapes, such as, but not limited to, narrow glass tubes.

BRIEF DESCRIPTION OF THE DRAWINGS

The accompanying drawings, which are incorporated into and constitute a part of the specification, illustrate specific embodiments of the invention and, together with the general description of the invention, and the detailed description of the specific embodiments, serve to explain the principles of the invention.

DETAILED DESCRIPTION

Figure 1:
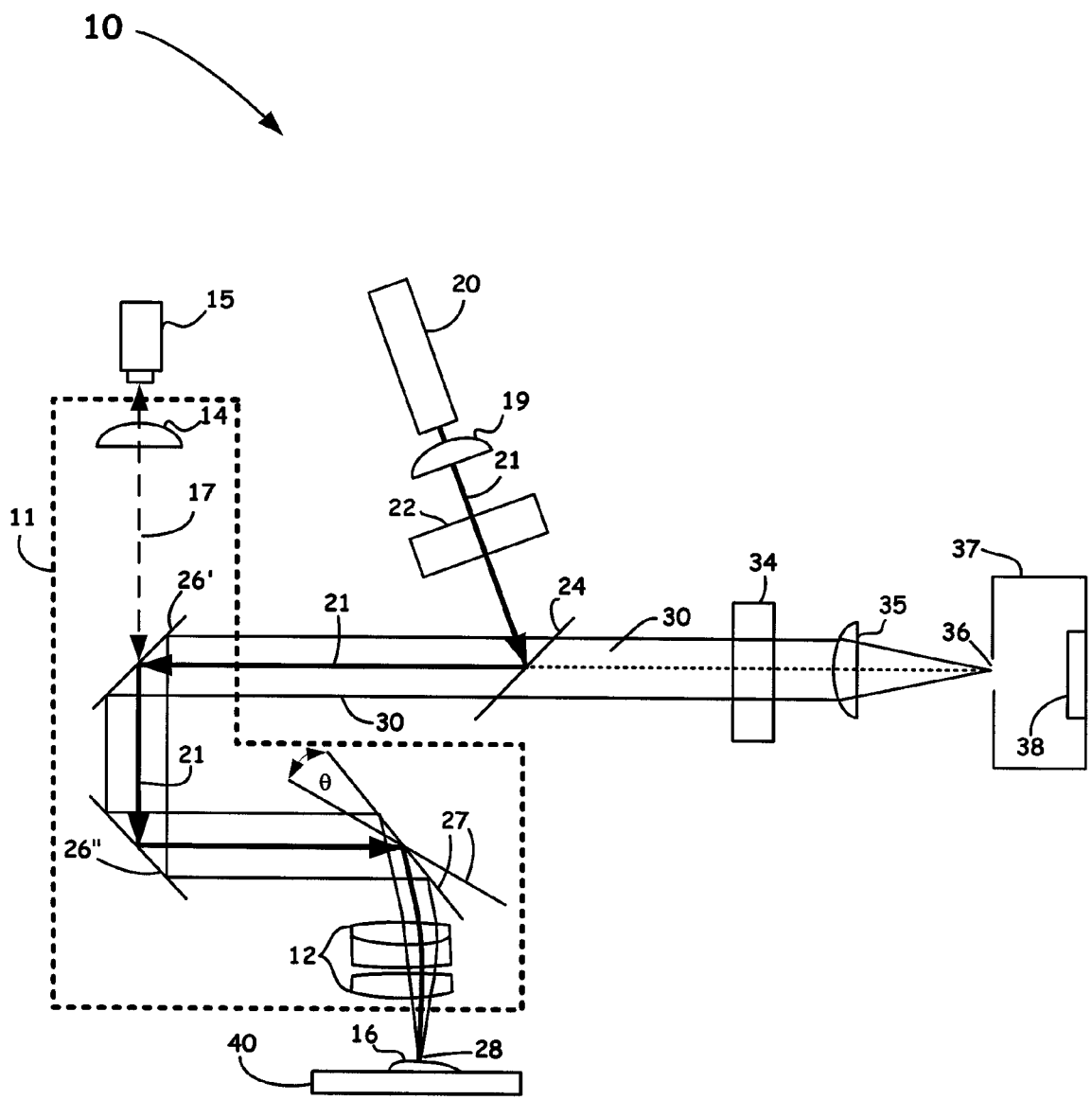
FIG. 1 shows a block diagram of a Raman Scanning system of the present invention.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise.

Moreover, unless otherwise indicated, numbers expressing quantities of ingredients, constituents, reaction conditions and so forth used in the specification and claims are to be understood as being modified by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

General Description

The present invention is directed to a spectroscopy spatial averaging method and apparatus, often a Raman spectroscopy spatial averaging method and apparatus. The configurations disclosed herein enable the instrument to remain in focus while the combined beam paths of the optical excitation source and the spectrograph are rapidly scanned in one or two dimensions along the surface of an interrogated sample.

Rapidly scanning the focal region about a plane, as disclosed herein, reduces the average radiation exposure to any given point on the sample and thus minimizes or eliminates sample damage (e.g., photodecomposition, thermal, or chemical) that can result from directed high-intensity beams. Thus, lateral as well as depth resolution can be achieved with the present invention to less than a micron (depending on the illumination wavelength and optical components) to analyze micro quantities of materials (e.g., films, powders, solutions, gases, and many other homogeneous and inhomogeneous materials that comprise Raman active molecules and structures) without any or minimal sample preparation and without any destruction.

It is to be appreciated that the scanning method of the present invention occurs in such a way that optimum focusing and light collection are retained while directing the focal point of the system's objective approximately about a desired plane. In particular, the scanning speed of the mirror can be neglected compared to the speed of light when using the disclosed optical sources and from such an arrangement the induced emission can be collected by the objective and returned along the original illumination path to its conjugate focal plane at the detector with sufficient magnitude. It is also to be appreciated that the configurations and methods of the present invention enable variations in the averaged signal intensity illuminating the detector aperture to correspond to variations in emission at localized points in the interrogated sample as the exciting beam is scanned.

Specific Description

Turning now to the drawings, FIG. 1 shows a spectroscopic scanning microscope system, generally designated by the reference numeral 10. Such a similar system is described in U.S. Pat. No. 6,661,509 B2, entitled, "Method And Apparatus For Alignment Of Multiple Beam Paths In Spectroscopy," to Deck et al., the disclosure of which is incorporated by reference in its entirety.

System 10 is beneficially applicable to Raman spectroscopy. However, the invention may be used for other applications, such as, but not limited to, laser-excited fluorescence spectrometers, which face similar issues solvable by the present invention and any laser-excited measurement instrument, such as, but not limited to laser-excited confocal fluorescence microscopes where sample burning or radiation damage is an issue.

The microscope system 10, often includes an optical microscope 11, as generally shown within the dashed lines labeled in FIG. 1. The microscope 11 includes an objective lens 12, often a lens comprised of a plurality of optical components (e.g., doublets, positive and negative lenses, etc.) designed to correct for chromatic and other optical aberrations which can have deleteriously effects on the collected desired emission signal strength as well as the directed illumination wavelengths. Moreover, lens 12 is designed to have a flat focal plane, a real entrance pupil located at a distance that provides mechanical clearance of up to about 15 mm for adjacent architecture, and a long working distance of up to about 17 mm from the rear surface of the lens to the sample plane for convenient routine use.

A beneficial and novel arrangement of the present invention includes an optical element that is directed about an axis so as to provide an angular displacement (denoted by θ and the accompanying double sided arrows) of any desired incoming radiation. In particular, the optical element often is configured as a moveable reflector (e.g., a MEMS mirror, a galvanometer, piezoelectric device, etc) 27, or often a pair of moveable mirrors, each to scan a desired axis, which can either be electrically and/or magnetically driven in a desired axis at up to about 100 Hz (note: the two axis are often driven at different frequencies ratios, e.g., ratios of 5:7). Such a reflector(s) 27, which is configured adjacent the objective lens 12, thus can provide angularly displaced radiation that enables spatial displacement by the objective lens 12 at up to about 5 mm about the deigned beam path, as shown in FIG. 1.

Figure 2:
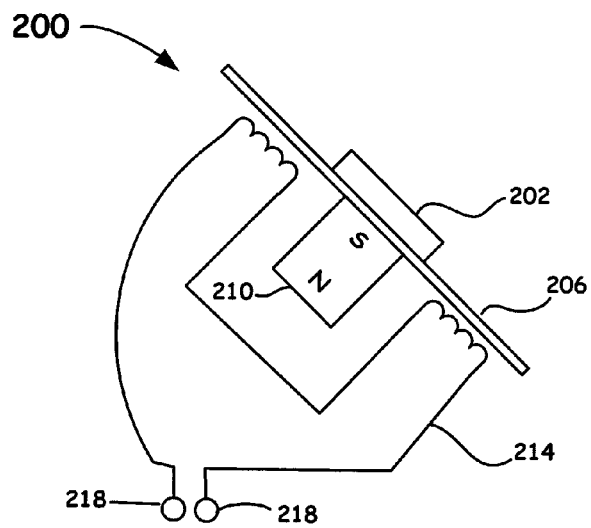
FIG. 2 shows a simple design of a moveable mirror utilized in the present invention.

FIG. 2 shows a beneficial example a single moveable reflector (e.g., a galvanometer), generally designated by the reference numeral 200 that can be utilized in the present invention. However, it is to be appreciated that the single mirror design shown in FIG. 2, while a beneficial embodiment, is to only illustrate a capability of the present invention, as a pair of such mirrors can also be configured to scan separate axis. Turning back to the example embodiment shown in FIG. 2, a reflective surface 202 designed for optical illumination wavelengths as well as for induced radiation from a sample, in such an example arrangement, can be held by flexible diaphragm 206, sometimes referred to as a "spider," which allows the mirror to tilt in angular directions with minimal overall displacement. A magnet 210 coupled to the back of the mirror 202 enables the reflector 200 to be driven by coils 214 (note: only one set of coils shown here for simplicity) in predetermined directions, i.e., along a designated X or Y axis. Electronic circuitry (not shown) as understood by those of ordinary skill in the art can be configured to provide drive signals to the coils input leads 218. Such signals can include, but are not limited to, sine, square, rectangular, linear, or random or pseudorandom signals.

Turning back to FIG. 1, it is to be appreciated that the objective lens 12 is designed to have large Numerical Aperture (N.A.) of up to about 0.5 thereby collecting an extremely large cone angle, often an N.A. of between 0.25 and 0.5 that enables a maximum a range of angles to be received from the moveable reflector(s) 27 without vignetting. The objective lens 12 thus can receive such angularly displaced radiation and can translate this angular displacement into a spatial displacement at the sample 16 while holding the focal region 28 approximately in a plane. If the objective has a focal length f, and the moveable reflector(s) 27, can direct an angular range of $\alpha$, then a dimensional size of the sampling area is $f\alpha$.

Also, as shown in FIG. 1, the microscope 11 often includes an ocular lens or lenses 14 which may be utilized for direct viewing by an observer (not shown) or which can be configured to provide for an image so as to be capable of being observed via may a video camera 15, wherein such optical information can be stored and manipulated by way of a computational system, e.g., a computer. Light from a scanned sample 16 is thus passed back through the objective lens 12 to the ocular lenses 14 on a beam path 17 (initially shown as a dashed line with accompanying double-directional arrows) in a conventional fashion to form an image that can be viewed by the operator either directly or imaged via a video camera 15 and accompanying conventional optics and instruments.

In the example microscope system illustrated in FIG. 1, electromagnetic energy is provided by an optical source 20, typically a laser, such as, but not limited to, a pulsed or Continuous Wave (CW) gas and/or a solid state device configured to emit polarized, e.g., linear, circular or elliptical polarization, or unpolarized radiation. Electromagnetic energy from source 20 thus is directed on an illuminating beam path 21 (illustrated as a heavier line weight with accompanying arrows to show the beam path) having a desired intensity using one or more beam shaping optics 19 through a beam path adjustment unit 22 (see incorporated by reference U.S. Pat. No. 6,661,509 B2 for a more detailed explanation) and such energy is received by a beam combining dichroic 24, often a notch filter, which is an optical element (often a holographic optical element) designed to reflect illumination wavelengths (e.g., Rayleigh scattered light) while transmitting desired Raman scattered light, often light comprised of wavelengths longer than the laser wavelength so as to be collected by a detector 38 of the present invention.

The detector 38 can thus include any equivalent means of spectral acquisition such as, but not limited to, a two-dimensional array detector, a multi-array detector, an on-chip amplification CCD camera, a back-illuminated, liquid nitrogen cooled CCD detector, a photomultiplier, an avalanche photodiode, and/or a photodiode. In addition, the detector 38 is capable of being configured with bandpass and/or polarization filters to acquire the various imaging modalities (e.g., desired fluorescence but more often Raman scattered spectra of polarized and/or unpolarized light). The detector output is coupled to a processor (not shown) to compare collected spectra so as to often help a user identify, analyze, and assess resultant spectra found in interrogated samples, such as, for example, films, powders, solutions, gases, drugs, food, tissue, or any homogeneous or inhomogeneous Raman active material desired to be examined in an expedient manner. The processor, such as a computer, thus performs many functions such as smoothing, spectral matching by means of an integrated library, digital filtering, wavelength calibration, instrument response correction, line-shape analysis, and/or signal averaging.

Turning back to FIG. 1, notch filter 24 thus can direct the illuminating beam 21 on a path toward one or more directing optics 26' and 26". The directing optics 26' and 26", designed to reflect the illumination wavelengths of the optical source 20 as well as the induced Raman longer wavelengths, may be formed as a plane mirror, e.g., a multilayer dielectric plane mirror, mounted on a conventional motorized means for selectable insertion into and removal out of the microscope optical beam path 17. When the directing optics 26' and 26" are moved into position in the beam path 17, they can direct the illuminating beam 21 onto a beam path which is collinear with the microscope optical beam path 17. The objective lens 12 thus focuses the illumination beam onto a focal region 28 having a predetermined intensity so as to induce Raman scattered light resulting from the scanned sample 16 mounted on a stage 40.

The microscope system also includes an induced return beam path, more often, a Raman return beam path 30, which is comprised of the scattered light to be collected by the objective lens 12 and formed into a collimated beam that can be manipulated by the directing mirrors 26' and 26" onto a path collinear with the illuminating beam path 21 up to the position of the notch filter 24. The notch filter 24, as discussed above, is designed to thus transmit the wavelengths of induced Raman radiation in the beam 30 and to preclude Rayleigh radiation resulting from the illuminating beam 21. After passing through the notch filter 24, the Raman radiation directed on the beam path 30 passes through a second beam path adjustment means 34 and through one or more optical elements, such as a refractive input lens 35, which can focus the beam 30 onto a desired input aperture 36 of a spectrograph 37. Following rays backwards through the system, from the spectrograph to the sample, the spectrograph 37 thus is configured to optically image a point of interest on the sample. This point on the sample, and the spectrograph input aperture 36, are conjugate points of a compound optic that comprises the objective 12 and the spectrograph input lens 35.

Accordingly, the spectrograph 37, as known to those skilled in the art of spectroscopy, spatially distributes the wavelengths of the induced radiation received in the beam 30 so as to be received by a detector 38 to detect the intensity of the light (e.g., Raman light) at the various wavelengths and thus provide an output spectrally resolved signal indicative of, for example, the Raman spectrum of detected compounds in a sample 16 under interrogation.

In a method of configuring the system 10, as shown in FIG. 1, the optics are aligned so that the optical source 20 is brought to a focus at the same point of interest. From such a process, the optical source 20 and the spectrograph 37 are looking at the same point. This is achieved by aligning the laser beam to be parallel with the spectrograph beam in the shared beam path, i.e., path 30, as shown in FIG. 1. The optical source 20 and spectrograph beams 30 are thus designed to be substantially parallel in the shared beam path, and thus the two beams focus to the same point, no matter what happens with the objective or the steering of the moveable reflector(s) 27, e.g., galvanometer mirrors, because they are optically the same beam path.

Because of such a parallel arrangement, tilting moveable reflector(s) 27 away from a center position results in the following: 1) The laser is focused to a spot on the sample 16 at a distance away from the nominal center of the sample 16. 2) The laser focus spot 28 becomes a point source for Raman-scattered radiation. 3) This radiation is collected by the objective lens 12, and returns along a path parallel to the laser beam, and hence, when it reaches the beam combiner, i.e., notch filter 24, such induced radiation is parallel with the spectrograph beam path. Therefore, when the galvanometer moves, the laser spot and spectrograph point of interest move together in a substantially exact manner.

Spatial Averaging:

As known to those of ordinary skill in the art, the Raman scattering process is instantaneous, because a photon is typically not absorbed by the sample. Thus, so long as the moveable reflector(s) 27 is moving at moderate speeds, there is effectively no time delay between the optical source 20 being directed to the sample 16 by the moveable reflector(s) 27, and returning to the spectrograph 37 on its way back through the moveable reflector(s) 27. Thus, wiggling, i.e., scanning the moveable reflector 2, (a galvanometer) at a moderate frequency has the same affect of a synchronized optical source 20 and spectrograph beam path.

Accordingly, in the present invention:

1. The spectrograph 37 performs a time exposure on its detector 38. Collecting light over a single exposure, or over multiple exposures summed together, represents a summing function. Since a time average is simply a sum divided by the overall collection time, the spectrograph 37 disclosed herein is performing time-averaging of the input spectrum.
2. If waveforms (sinusoids, random or pseudorandom signals, or any other kind of drive signal, or even pure noise) are applied to at least one of the moveable reflector(s) 27 coils, then the position of the shared focus spot at the sample 16 becomes a function of time.
3. Position is a function of time, and the spectrograph performs a time-average, so that the combined effect is a spatial average over points along the path that the focus spot follows on the sample.

In such an arrangement, neither the laser nor the spectrograph beam paths are ever out of focus. Thus, there is no substantial loss of intensity for the Raman spectrum, and hence no degradation of signal-to-noise, when the moveable reflector(s) 27, i.e., the galvanometer, is scanned. In practice, there could be a small amount of loss due to vignetting or optical aberrations, but such losses are minor compared to any scheme involving defocusing of the optical source or spectrograph, or schemes where the magnification of the laser or spectrograph beams are significantly different. This is a considerable benefit of the present invention.

In a method of operation using the configuration shown in FIG. 1, the motors that are configured with the moveable reflector(s) 27 to direct rays along a particular axis can be driven by sine waves whose frequency ratio is the ratio of small numbers that are relatively prime. A beneficial design uses a 5:7 ratio, however other ratios that can provide spectra of compounds in samples of interest are equally capable of being utilized without departing from the scope of the present invention. The resulting pattern using sine waves on the sample is a Lissajous figure. However, in other beneficial arrangements, the amplitudes of the two axes can be independently varied to allow patterns that appear to be approximately a square, a rectangle, a triangle, a hexagon, a random pattern, or a predetermined pattern, such as a linear pattern, based on the drive frequencies. A linear pattern is potentially useful for looking at samples in narrow capillary tubes. Being able to adjust the pattern electronically allows the user to conveniently set up the instrument for different sizes of samples. The user selects dimensions for the beam pattern on the sample. Then the instrument collects a time exposure as if it were a single homogeneous sample. The resulting displayed spectrum represents a spatial average over the sample.

In the present example, the objective lens collected Raman scattered light at an N.A. of at least 0.25, with a preferred N.A. of between 0.25 up to about 0.5, with a long working distance of about 17 mm. The moveable reflector distance to the first lens element of the objective measured about 15 mm. However, while such a lens and distances are beneficial, it is to be understood that the present invention is not limited to any particular lens and working distance parameters. Accordingly, optical as well as mechanical design parameters can be manipulated so as to optimize the system presented herein for a given application.

The present invention will be more fully understood by reference to the following experimental results, which are intended to be illustrative of the present invention, but not limiting thereof.

Figure 3:
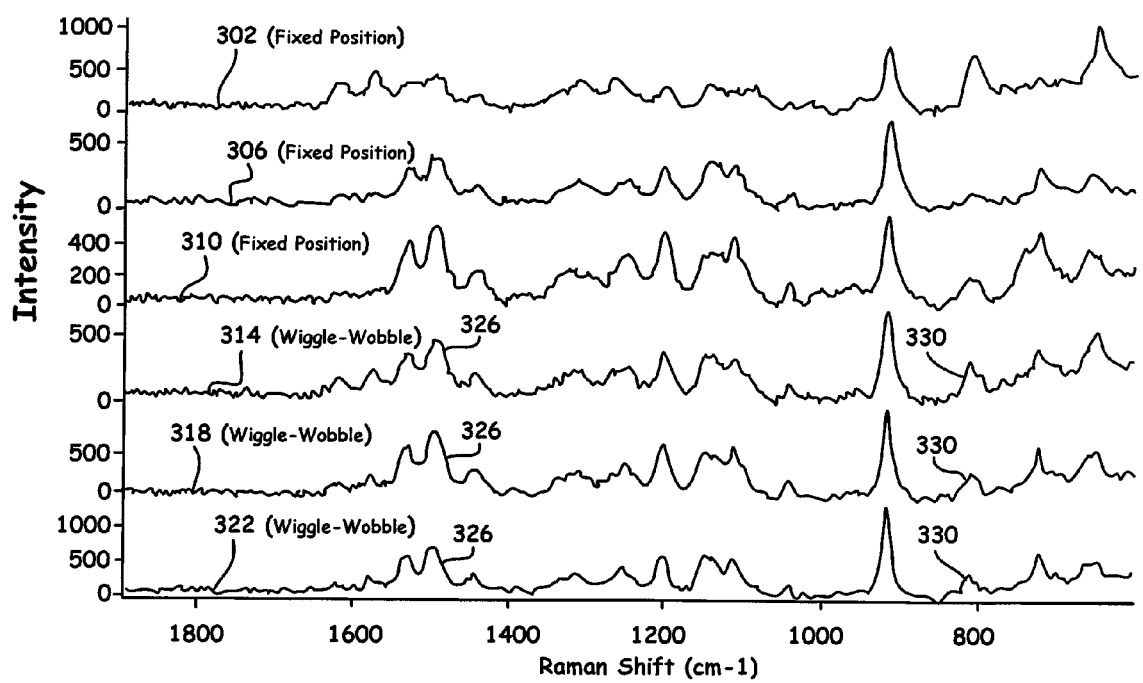
FIG. 3 illustrates experimental results of detected compounds in an interrogated sample.

Example Experimental Results:

FIG. 3 shows example experimental Raman spectral data resulting from an interrogated orange Alka-Seltzer sample so as to demonstrate the concept of the invention. Thus, as shown in FIG. 3, the first three spectra, as denoted by the reference numerals 302, 306, and 310, are obtained by allowing the system to sit fixed at three different positions (i.e., non-scanned spectra). The second three spectra, as denoted by the reference numerals 314, 318, and 322, are obtained by scanning (using sine drive signals of about 60 Hz) the focused laser spot about a line displacement of up to about 5 mm via the moveable reflector, as shown in FIG. 2. As illustrated in FIG. 3, there are two distinct peaks of sufficient intensity at about 800 (as denoted by the reference numeral 330) and 1500 $cm^{-1}$ (as denoted by the reference numeral 326) visible in the scanned spectra (i.e., the scanning test positions, 314, 318, and 322), which suggests the presence of two different compounds. However, such peaks are not distinct in each of the fixed position spectra (e.g., fixed position spectra 306). Thus, the example spectra illustrates that the scanning technique for interrogating a sample is beneficial when such compounds may be localized (i.e., heterogeneous) within a sample area.

It is to be understood that features described with regard to the various embodiments herein may be mixed and matched in any combination without departing from the spirit and scope of the invention. Although different selected embodiments have been illustrated and described in detail, it is to be appreciated that they are exemplary, and that a variety of substitutions and alterations are possible without departing from the spirit and scope of the present invention, as defined by the following claims.

The invention claimed is:

1. A spatially averaging Raman optical microscope, comprising:
   an illumination source;
   an objective lens configured to focus and spatially displace upon a sample, received X-Y angularly displaced light of said illumination source so as to induce Raman light, said objective lens being further configured to substantially spatially collect and direct said induced Raman light along a predetermined Raman beam path so that said Raman light can be detected and spectrally resolved;
   at least one X-Y scanning mirror interposed between said illumination source and said objective lens, said X-Y scanning mirror being configured to receive drive signals in a prime ratio so that received radiation from said illumination source can be angularly displaced on said objective lens so as to scan in a time-dependent manner, a desired area of said sample with said illumination source; and
   detection and analyzing means configured to collect and spectrally resolve in a spatially averaged manner, said induced Raman light.

2. The microscope of claim 1, wherein said sample comprises an inhomogeneous Raman active material.

3. The microscope of claim 1, wherein said sample comprises a homogeneous Raman active material.

4. The microscope of claim 1, wherein said sample comprises at least one Raman active material selected from: films, powders, solutions, gases, drugs, food, and tissue.

5. The microscope of claim 1, wherein collection of said spatially averaged spectrally resolved Raman light is less than about 1 second.

6. The microscope of claim 1, wherein said prime ratio is 5:7.

7. The microscope of claim 1, wherein said received drive signals comprises a range of less than about 100 Hz.

8. The microscope of claim 1, wherein said received drive signals comprise at least one drive signal selected from: sinusoids, random signals, pseudorandom signals, and noise.

9. The microscope of claim 7, wherein said drive signals results in at least one illumination pattern upon the sample selected from: a square, a rectangle, a triangle, a hexagon, a random pattern, and a predetermined pattern based on the drive frequencies.

10. The microscope of claim 1, wherein a programmed dimension of said desired scanned area comprises a range of up to about 5 mm.

11. The microscope of claim 1, wherein said objective lens comprises a plurality of optical surfaces to produce a Numerical Aperture (N.A.) of between about 0.25 up to about 0.5.

12. The microscope of claim 1, wherein a working distance between the last surface of said objective lens to a sample plane comprises a range of up to about 17 mm.

13. The microscope of claim 1, wherein said focal region produced by said objective lens and an aperture configured with said detection means are conjugate optical planes to provide for a confocal configuration.

14. A Raman spatially averaging method, comprising:
   providing drive signals in a prime ratio to at least one X-Y scanning mirror so that an angularly displaced beam of light from an illumination source can be produced;
   spatially displacing via a focusing objective lens, said angularly displaced illumination beam of light so that a desired area of a sample can be scanned to induce Raman light in a time dependent manner; and
   spatially averaging a detected said induced Raman light from said scanned desired area so that spectrally resolved information can be assessed.

15. The Raman spatially averaging method of claim 14, wherein said sample comprises an inhomogeneous Raman active material.

16. The Raman spatially averaging method of claim 14, wherein said sample comprises a homogeneous Raman active material.

17. The Raman spatially averaging method of claim 14, wherein said sample comprises at least one Raman active material selected from: films, powders, solutions, gases, drugs, food, and tissue.

18. The Raman spatially averaging method of claim 14, further comprising: collecting said spectrally resolved information in less than about 1 second.

19. The Raman spatially averaging method of claim 14, further comprising: providing drive signals in a prime ratio of 5:7.

20. The Raman spatially averaging method of claim 14, further comprising: providing drive signals of less than about 100 Hz.

21. The Raman spatially averaging method of claim 14, further comprising: providing at least one drive signal selected from: sinusoids, random signals, pseudorandom signals, and noise.

22. The Raman spatially averaging method of claim 14, further comprising: providing a programmed dimension to scan said desired scanned area in a range of up to about 5 mm.

* * * * *